United States Patent [19]

Kmiec et al.

[11] Patent Number: 5,691,187
[45] Date of Patent: Nov. 25, 1997

[54] ANTI-FUNGAL AGENTS AND METHODS OF IDENTIFYING AND USING THE SAME

[75] Inventors: Eric B. Kmiec, Malvern; David L. Gerhold, Huntingdon Valley; Allyson Cole Strauss, Philadelphia, all of Pa.

[73] Assignee: Thomas Jefferson University, Philadelphia, Pa.

[21] Appl. No.: 485,621

[22] Filed: Jun. 7, 1995

[51] Int. Cl.$^6$ .............. C12N 15/61; C12N 15/63; C12N 1/14; C12N 1/16; C12N 1/18; C12N 5/10; C12N 1/21

[52] U.S. Cl. .............. 435/252.3; 435/320.1; 435/254.11; 435/325; 435/410; 435/252.33; 435/254.21; 536/232

[58] Field of Search ................. 435/320.1, 240.1, 435/252.3, 254.11, 252.33, 254.2, 254.21, 325, 410; 536/23.2, 24.3, 24.32, 24.33

[56] References Cited

U.S. PATENT DOCUMENTS 4,736,866  4/1988  Leder et al. ................. 800/2
4,873,191  10/1989  Wagner et al. ............ 435/172.3

OTHER PUBLICATIONS

Fostel et al. "Characterization of DNA Topoisomerase I from *Candida albicans* as a target for drug discovery". Antimicrobial Agents and Chemotherapy 36(10):2131–2138, Oct. 1992.

Shen et al., "DNA topoisomerase inhibitors as antifungal agents." Advances in Pharmacology 29B:227–244, 1994.

Taylor, et al., "Identification of the gene encoding DNA topoisomerase I from *Candida albicans*", *FEMS Microbiology Letters*, 1996, 138, 113–121.

Bjournsti, et al., "Expression of Human DNA Topoisomerase I in Yeast Cells Lacking Yeast DNA Topoisomerase I: Restoration of Sensitivity of the Cells to the Antitumor Drug Camptothecin[1]", *Cancer Research*, 49, 6318–6323 (1989).

Elble, R., "A Simple and Efficient Procedure for Transformation of Yeasts", *Biotechniques*, 13(1), 18–20 (1992).

Thrash, et al., "Cloning, characterization, and sequence of the yeast DNA topoisomerase I gene", *Proc. Natl. Acad. Sci. USA*, 82, 4374–4378 (1985).

*Primary Examiner*—Robert A. Wax
*Assistant Examiner*—G. E. Bugaisky
*Attorney, Agent, or Firm*—Woodcock Washburn Kurtz Mackiewicz & Norris LLP

[57] ABSTRACT

Substantially pure *C. albicans* topoisomerase I protein is disclosed. Nucleic acid molecules that encode *C. albicans* topoisomerase I protein, recombinant expression vectors that comprise a nucleic acid sequence that encodes *C. albicans* topoisomerase I protein, and host cells that comprise recombinant expression vectors that comprise nucleic acid sequences that encode *C. albicans* topoisomerase I protein are disclosed. Fragments of nucleic acid molecules with sequences encoding *C. albicans* topoisomerase I protein and oligonucleotide molecules that comprise a nucleotide sequence complimentary to fragment of a nucleotide sequence that encodes *C. albicans* topoisomerase I protein are disclosed. Antibodies which bind to an epitope on *C. albicans* topoisomerase I protein are disclosed. Methods of identifying inhibitors of *C. albicans* topoisomerase I protein are disclosed.

9 Claims, No Drawings

SEQUENCE LISTING ( 1 ) GENERAL INFORMATION:

( i i i ) NUMBER OF SEQUENCES: 2

( 2 ) INFORMATION FOR SEQ ID NO:1:

( i ) SEQUENCE CHARACTERISTICS:
        ( A ) LENGTH: 3143 base pairs
        ( B ) TYPE: nucleic acid
        ( C ) STRANDEDNESS: double
        ( D ) TOPOLOGY: unknown ( i i ) MOLECULE TYPE: genomic DNA -continued ( i x ) FEATURE:
    ( A ) NAME/KEY: CDS
    ( B ) LOCATION: 547..2889

( x i ) SEQUENCE DESCRIPTION: SEQ ID NO:1:

```
GAATTCCTCA AACACGGTCA AAAAAATACC AACTATCTTC TGTTTCTCCC CACTCACACG      60

ACCCAACTAT TTTTTTGGTG ATGGTTTTAG GCGCGACGTT AATCATTTTT ACTATTGAGA     120

ATGATTACTC CCACATTCTA TTACACCTCA TCTTCATCTT CATCTTTCAT CTTTCACATC     180

ACTAAATATA ACCTTGCGAC CTTCACAAAT TTTTTTTTT  GACAAGCAAT CCAAAATTAC     240

AATTTCATT  TCATTTCTTT TATATATAAA AGTTTTCAC  CATTAATTTC ACCACACATC     300

TCATTAGCAA TTGGGCAAAA ATAGAAAGTA ATTTATAAC  TTATAACCAA AAACAATTCA     360

AGAACAATAT CATTATTATT AAATTTATCA CGGAATTTGT TTTGCAAATC AAGTAAGAAC     420

AATTTCCATC AATTTACTCA TCAGTTTGGT TGTAATAATA AAAACAGATT ATTTTTCTTA     480

TCATCACCAC CAAGAGTATT CCGTTATTTA AATCCATTAT TTGTTCGTTC ATATAGCATA     540

ATTCCT ATG AGT TCA TCA GAC GAA GAA GAC ATT GCC TTG TCT AGA CTC       588
       Met Ser Ser Ser Asp Glu Glu Asp Ile Ala Leu Ser Arg Leu
        1               5                      10

GCT AAA AAA TCA TCC TCG ATC ACT TCA GCT TCC ACT TAT GAA GAC GAT       636
Ala Lys Lys Ser Ser Ser Ile Thr Ser Ala Ser Thr Tyr Glu Asp Asp
 15              20                  25                  30

GAA GAT GAT GAT ATC CCT TTA GCT AAA AAA TCC AGG AAA AAG AGG GTT       684
Glu Asp Asp Asp Ile Pro Leu Ala Lys Lys Ser Arg Lys Lys Arg Val
                 35              40                  45

GAA TCT GAT TAT GAA GAA GAT GAA GAC GAA GTC CCA TTG AAA AAG AGA       732
Glu Ser Asp Tyr Glu Glu Asp Glu Asp Glu Val Pro Leu Lys Lys Arg
             50                  55                  60

AAA TTG TCT AAT GGT AGA GCA AAA AAA CAA GTT AAA ACC GAA ACT AAA       780
Lys Leu Ser Asn Gly Arg Ala Lys Lys Gln Val Lys Thr Glu Thr Lys
         65                  70                  75

GTT AAA AAG GAA CCT AAA AGT GCC AAT AAA TCC AAA TCT ACA TCT AAA       828
Val Lys Lys Glu Pro Lys Ser Ala Asn Lys Ser Lys Ser Thr Ser Lys
     80                  85                  90

AAG GAC ACC AAA GTT AAG AAA GAG AAA ACT ACA GTC AAG AAG GAA TCT       876
Lys Asp Thr Lys Val Lys Lys Glu Lys Thr Thr Val Lys Lys Glu Ser
 95                 100                 105                 110

AAA GCC ACA AGC ACT AAA GTG AAA GAA GAA TCC AAA ACT CAA TCA GAT       924
Lys Ala Thr Ser Thr Lys Val Lys Glu Glu Ser Lys Thr Gln Ser Asp
                115                 120                 125

TCA CAA GCA TCG GTT AAA TCT GAA ACT CCT GAA GAA GAT CAA GGG TAC       972
Ser Gln Ala Ser Val Lys Ser Glu Thr Pro Glu Glu Asp Gln Gly Tyr
            130                 135                 140

AAA TGG TGG GAA GTG AAT CAA GAA GAA GAA GGT GAT GGT TAT ATC AAA      1020
Lys Trp Trp Glu Val Asn Gln Glu Glu Glu Gly Asp Gly Tyr Ile Lys
        145                 150                 155

TGG CAA ACA CTA GAA CAT AAC GGT GTT ATG TTT CCA CCA CCA TAT GAA      1068
Trp Gln Thr Leu Glu His Asn Gly Val Met Phe Pro Pro Pro Tyr Glu
160             165                 170

CCA TTA CCA TCT CAT GTC AAA TTA TAT TAT AAC AAT AAA CCA GTT AAT      1116
Pro Leu Pro Ser His Val Lys Leu Tyr Tyr Asn Asn Lys Pro Val Asn
175             180                 185                 190

TTA CCT CCA GAA GCA GAA GAA GTT GCC GGA TTT TAT GGA GCA ATG TTA      1164
Leu Pro Pro Glu Ala Glu Glu Val Ala Gly Phe Tyr Gly Ala Met Leu
                195                 200                 205

GAA ACT GAT CAT GCT AAA AAC CCA GTT TTC CAA AAG AAT TTT TTC AAT      1212
Glu Thr Asp His Ala Lys Asn Pro Val Phe Gln Lys Asn Phe Phe Asn
            210                 215                 220
```

| | | | | | | | | | | | | | | | | |
|---|---|---|---|---|---|---|---|---|---|---|---|---|---|---|---|---|
| GAT | TTT | TTG | GAA | GTT | TTA | AAA | GAA | TGT | GGT | GGT | TGT | GGT | GTT | GAA | ATT | 1260 |
| Asp | Phe | Leu 225 | Glu | Val | Leu | Lys | Glu 230 | Cys | Gly | Gly | Cys 235 | Gly | Val | Glu | Ile | |
| AAA | AAA | TTT | GAA | AAA | TTA | GAT | TTT | AGT | AAA | ATG | TAT | GCT | CAT | TTT | GAA | 1308 |
| Lys | Lys 240 | Phe | Glu | Lys | Leu | Asp 245 | Phe | Ser | Lys | Met | Tyr 250 | Ala | His | Phe | Glu | |
| AAA | TTA | CGT | GAA | GAG | AAA | AAG | GCC | ATG | AGT | AGG | GAA | GAA | AAG | AAA | AGA | 1356 |
| Lys 255 | Leu | Arg | Glu | Glu | Lys 260 | Lys | Ala | Met | Ser 265 | Arg | Glu | Glu | Lys | Lys | Arg 270 | |
| ATC | AAA | GAA | GAA | AAA | GAA | AAA | GAA | GAA | GAA | CCT | TAT | AGG | ACT | TGT | TAT | 1404 |
| Ile | Lys | Glu | Glu | Lys 275 | Glu | Lys | Glu | Glu | Glu 280 | Pro | Tyr | Arg | Thr | Cys 285 | Tyr | |
| CTT | AAT | GGT | AGA | AAA | GAA | TTA | GTG | GGG | AAT | TTC | CGT | ATT | GAA | CCT | CCA | 1452 |
| Leu | Asn | Gly | Arg 290 | Lys | Glu | Leu | Val | Gly 295 | Asn | Phe | Arg | Ile | Glu 300 | Pro | Pro | |
| GGT | TTA | TTC | CGT | GGT | CGT | GGT | GCA | CAT | CCT | AAA | ACT | GGG | AAA | TTA | AAA | 1500 |
| Gly | Leu | Phe 305 | Arg | Gly | Arg | Gly | Ala 310 | His | Pro | Lys | Thr | Gly 315 | Lys | Leu | Lys | |
| CGT | CGA | GTA | GTG | CTG | GAA | CAA | GTG | ACT | TTG | AAT | TTA | GGT | AAA | GAT | GCT | 1548 |
| Arg | Arg 320 | Val | Val | Leu | Glu | Gln 325 | Val | Thr | Leu | Asn | Leu 330 | Gly | Lys | Asp | Ala | |
| AAA | ATA | CCT | GAA | CCA | CCT | GCA | GGC | CAT | CAA | TGG | GGG | GAA | ATT | AGA | CAT | 1596 |
| Lys 335 | Ile | Pro | Glu | Pro | Pro 340 | Ala | Gly | His | Gln | Trp 345 | Gly | Glu | Ile | Arg | His 350 | |
| GAT | AAT | GAA | GTC | ACT | TGG | TTA | GCC | ATG | TGG | AAA | GAA | AAT | ATT | TCT | GAT | 1644 |
| Asp | Asn | Glu | Val | Thr 355 | Trp | Leu | Ala | Met | Trp 360 | Lys | Glu | Asn | Ile | Ser 365 | Asp | |
| TCA | TTG | AAA | TAC | GTT | AGA | TTT | GCT | AAT | AAT | TCT | TCA | GTT | AAA | GGT | CAA | 1692 |
| Ser | Leu | Lys | Tyr 370 | Val | Arg | Phe | Ala | Asn 375 | Asn | Ser | Ser | Val | Lys 380 | Gly | Gln | |
| TCC | GAT | TTC | AAA | AAA | TTT | GAA | ACG | GCG | AGA | AAA | TTA | AGA | GAT | CAC | GTT | 1740 |
| Ser | Asp | Phe 385 | Lys | Lys | Phe | Glu | Thr 390 | Ala | Arg | Lys | Leu | Arg 395 | Asp | His | Val | |
| GAT | TCT | ATT | AGA | AAA | GAT | TAT | ACC | AAA | ATG | TTA | AAA | TCA | GAG | AAA | ATG | 1788 |
| Asp | Ser | Ile | Arg 400 | Lys | Asp | Tyr | Thr | Lys 405 | Met | Leu | Lys | Ser | Glu 410 | Lys | Met | |
| CAA | GAT | AGA | CAA | ATG | GCC | ACG | GCT | ATG | TAT | CTT | ATT | GAT | GTT | TTT | GCA | 1836 |
| Gln | Asp | Arg | Gln 415 | Met | Ala | Thr | Ala | Met 420 | Tyr | Leu | Ile | Asp 425 | Val | Phe | Ala 430 | |
| TTG | AGG | GCT | GGT | GGT | GAA | AAA | GGT | GAG | GAT | GAA | GCC | GAT | ACC | GTT | GGT | 1884 |
| Leu | Arg | Ala | Gly | Gly 435 | Glu | Lys | Gly | Glu | Asp 440 | Glu | Ala | Asp | Thr | Val 445 | Gly | |
| TGT | TGT | TCA | TTA | CGA | TAT | GAA | CAT | GTA | ACT | TTA | AAA | CCA | CCC | AAC | AAG | 1932 |
| Cys | Cys | Ser | Leu 450 | Arg | Tyr | Glu | His | Val 455 | Thr | Leu | Lys | Pro | Pro 460 | Asn | Lys | |
| GTT | ATT | TTC | GAT | TTT | TTG | GGT | AAA | GAT | TCA | ATT | AGA | TTT | TAT | CAA | GAA | 1980 |
| Val | Ile | Phe 465 | Asp | Phe | Leu | Gly | Lys 470 | Asp | Ser | Ile | Arg | Phe 475 | Tyr | Gln | Glu | |
| GTT | GAA | GTT | GAT | AAA | CAA | GTT | TTC | AAA | AAT | CTA | CGA | ATT | TTC | AAA | AAA | 2028 |
| Val | Glu | Val | Asp 480 | Lys | Gln | Val | Phe | Lys 485 | Asn | Leu | Arg | Ile | Phe 490 | Lys | Lys | |
| TCT | CCT | AAA | CAA | CCT | GGT | GAT | GAT | TTA | TTT | GAT | CGT | ATA | AAC | CCT | TCA | 2076 |
| Ser | Pro | Lys | Gln 495 | Pro | Gly | Asp | Asp | Leu 500 | Phe | Asp | Arg | Ile | Asn 505 | Pro | Ser 510 | |
| TTA | GTC | AAT | CGA | CAA | TTA | CAA | AAT | TAT | ATG | AAA | GGA | TTA | ACA | GCA | AAA | 2124 |
| Leu | Val | Asn | Arg | Gln 515 | Leu | Gln | Asn | Tyr | Met 520 | Lys | Gly | Leu | Thr | Ala 525 | Lys | |
| GTT | TTC | CGT | ACA | TAT | AAT | GCC | TCG | AAA | ACC | ATG | CAA | GAT | CAA | ATT | GAT | 2172 |
| Val | Phe | Arg | Thr | Tyr 530 | Asn | Ala | Ser | Lys 535 | Thr | Met | Gln | Asp | Gln 540 | Ile | Asp | |

| | | | | | | | | | | | | | | | | |
|---|---|---|---|---|---|---|---|---|---|---|---|---|---|---|---|---|
| ATA | ATT | GAA | AAT | GAA | GGT | ACA | GTG | GCG | GAA | AAA | GTG | GCT | AAA | TTC | AAT | 2220 |
| Ile | Ile | Glu | Asn | Glu | Gly | Thr | Val | Ala | Glu | Lys | Val | Ala | Lys | Phe | Asn | |
| | | | 545 | | | | 550 | | | | | 555 | | | | |
| GCT | GCC | AAT | AGA | ACG | GTG | GCT | ATT | TTA | TGT | AAT | CAC | CAG | CGT | ACG | GTC | 2268 |
| Ala | Ala | Asn | Arg | Thr | Val | Ala | Ile | Leu | Cys | Asn | His | Gln | Arg | Thr | Val | |
| | | 560 | | | | | 565 | | | | 570 | | | | | |
| AGT | AAA | ACC | CAT | GGT | GAT | AGT | GTT | CAG | AGA | ATT | AAT | GAC | AAA | TTG | AAA | 2316 |
| Ser | Lys | Thr | His | Gly | Asp | Ser | Val | Gln | Arg | Ile | Asn | Asp | Lys | Leu | Lys | |
| 575 | | | | | 580 | | | | | 585 | | | | | 590 | |
| AAA | TTC | ATG | TGG | CAA | AAG | ATT | AGA | TTA | AAG | AAA | ATG | ATC | TTA | CAA | TTA | 2364 |
| Lys | Phe | Met | Trp | Gln | Lys | Ile | Arg | Leu | Lys | Lys | Met | Ile | Leu | Gln | Leu | |
| | | | | 595 | | | | | 600 | | | | | 605 | | |
| GAA | CCC | AAA | TTG | AAA | AAG | AAA | GAT | TCG | AAA | TAT | TTT | GAA | GAA | ATT | GAT | 2412 |
| Glu | Pro | Lys | Leu | Lys | Lys | Lys | Asp | Ser | Lys | Tyr | Phe | Glu | Glu | Ile | Asp | |
| | | | 610 | | | | | 615 | | | | | 620 | | | |
| GAT | TTA | CTC | AAA | GAA | GAT | ATT | GAA | CAT | ATT | CAT | CAT | ACT | ATA | ATT | AAA | 2460 |
| Asp | Leu | Leu | Lys | Glu | Asp | Ile | Glu | His | Ile | His | His | Thr | Ile | Ile | Lys | |
| | | 625 | | | | | 630 | | | | | 635 | | | | |
| AGA | CAA | CGA | GAA | CAA | GCT | AAA | AAA | AAA | TTA | GAA | CGT | GAT | AAT | GAA | AAA | 2508 |
| Arg | Gln | Arg | Glu | Gln | Ala | Lys | Lys | Lys | Leu | Glu | Arg | Asp | Asn | Glu | Lys | |
| | 640 | | | | | 645 | | | | | 650 | | | | | |
| TTG | AAA | CTT | GAA | GGT | AAA | CCA | TTA | TTA | ACT | GAA | TCA | GAT | ATA | AAA | GAT | 2556 |
| Leu | Lys | Leu | Glu | Gly | Lys | Pro | Leu | Leu | Thr | Glu | Ser | Asp | Ile | Lys | Asp | |
| 655 | | | | | 660 | | | | | 665 | | | | | 670 | |
| AAA | TTA | GAT | AAA | ATT | GAT | GAA | TTA | GAA | AAA | GAA | TAT | CAA | AAA | GAA | TTG | 2604 |
| Lys | Leu | Asp | Lys | Ile | Asp | Glu | Leu | Glu | Lys | Glu | Tyr | Gln | Lys | Glu | Leu | |
| | | | | 675 | | | | | 680 | | | | | 685 | | |
| AAA | ACT | GGT | AAA | CCA | ATA | GTC | ACC | AAA | AAT | GCT | ACC | GTT | GAA | AAA | TTA | 2652 |
| Lys | Thr | Gly | Lys | Pro | Ile | Val | Thr | Lys | Asn | Ala | Thr | Val | Glu | Lys | Leu | |
| | | | 690 | | | | | 695 | | | | | 700 | | | |
| AAA | CAA | CAA | ATT | GAA | ACT | CTT | GAA | AAT | AAA | ATT | CTT | AAT | GTT | TCA | ATT | 2700 |
| Lys | Gln | Gln | Ile | Glu | Thr | Leu | Glu | Asn | Lys | Ile | Leu | Asn | Val | Ser | Ile | |
| | | 705 | | | | | 710 | | | | | 715 | | | | |
| CAA | TTA | AAA | GAT | AAA | GAA | GAT | AAT | TCT | GAA | GTT | TCT | TTA | GGA | ACT | TCA | 2748 |
| Gln | Leu | Lys | Asp | Lys | Glu | Asp | Asn | Ser | Glu | Val | Ser | Leu | Gly | Thr | Ser | |
| | 720 | | | | | 725 | | | | | 730 | | | | | |
| AAA | ATG | AAT | TAT | ATT | GAT | CCA | AGA | TTA | ATT | GTT | ATG | TTT | TCT | AAA | AAA | 2796 |
| Lys | Met | Asn | Tyr | Ile | Asp | Pro | Arg | Leu | Ile | Val | Met | Phe | Ser | Lys | Lys | |
| 735 | | | | | 740 | | | | | 745 | | | | | 750 | |
| TTT | GAT | GTT | CCT | ATT | GAA | AAA | TTA | TTT | ACC | AAA | ACT | TTA | AGA | GAA | AAG | 2844 |
| Phe | Asp | Val | Pro | Ile | Glu | Lys | Leu | Phe | Thr | Lys | Thr | Leu | Arg | Glu | Lys | |
| | | | | 755 | | | | | 760 | | | | | 765 | | |
| TTC | ATT | TGG | GCT | ATT | GAA | TCA | GCT | GAT | GAA | AAT | TGG | AGA | TTC | TAA | | 2889 |
| Phe | Ile | Trp | Ala | Ile | Glu | Ser | Ala | Asp | Glu | Asn | Trp | Arg | Phe | * | | |
| | | | 770 | | | | | 775 | | | | | 780 | | | |

| | | | | | |
|---|---|---|---|---|---|
| AATTAGGGGT | TTGTTTCTTA | GCTTATTATT | ATATACTATA | TGCTGTAGAG | TAAAATTTTG | 2949 |
| TACCTTGTAA | TATATATATA | TACATTGTTT | CAACATAGAA | AAATAGATTG | ATACTGCAGT | 3009 |
| ATGAAAAAGA | ATATGCACAC | ACCAAGCAAG | TGTATTTTAG | ATAAAGGATT | GGTGTTTTGA | 3069 |
| TATTGGAAGG | GTGAAAGATG | AAGGGGGTAT | CACACAGACA | CGTACAATCA | AGAAATTGAA | 3129 |
| ATTTCTCCGA | ATTC | | | | | 3143 |

( 2 ) INFORMATION FOR SEQ ID NO:2:

( i ) SEQUENCE CHARACTERISTICS:
        ( A ) LENGTH: 780 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

| Met | Ser | Ser | Ser | Asp | Glu | Glu | Asp | Ile | Ala | Leu | Ser | Arg | Leu | Ala | Lys |
|---|---|---|---|---|---|---|---|---|---|---|---|---|---|---|---|
| 1 | | | | 5 | | | | | 10 | | | | | | 15 |

| Lys | Ser | Ser | Ser | Ile | Thr | Ser | Ala | Ser | Thr | Tyr | Glu | Asp | Asp | Glu | Asp |
|---|---|---|---|---|---|---|---|---|---|---|---|---|---|---|---|
| | | | 20 | | | | | 25 | | | | | 30 | | |

| Asp | Asp | Ile | Pro | Leu | Ala | Lys | Lys | Ser | Arg | Lys | Lys | Arg | Val | Glu | Ser |
|---|---|---|---|---|---|---|---|---|---|---|---|---|---|---|---|
| | | 35 | | | | | 40 | | | | | 45 | | | |

| Asp | Tyr | Glu | Glu | Asp | Glu | Asp | Glu | Val | Pro | Leu | Lys | Lys | Arg | Lys | Leu |
|---|---|---|---|---|---|---|---|---|---|---|---|---|---|---|---|
| | 50 | | | | | 55 | | | | | 60 | | | | |

| Ser | Asn | Gly | Arg | Ala | Lys | Lys | Gln | Val | Lys | Thr | Glu | Thr | Lys | Val | Lys |
|---|---|---|---|---|---|---|---|---|---|---|---|---|---|---|---|
| 65 | | | | | 70 | | | | | 75 | | | | | 80 |

| Lys | Glu | Pro | Lys | Ser | Ala | Asn | Lys | Ser | Lys | Ser | Thr | Ser | Lys | Lys | Asp |
|---|---|---|---|---|---|---|---|---|---|---|---|---|---|---|---|
| | | | | 85 | | | | | 90 | | | | | 95 | |

| Thr | Lys | Val | Lys | Lys | Glu | Lys | Thr | Thr | Val | Lys | Lys | Glu | Ser | Lys | Ala |
|---|---|---|---|---|---|---|---|---|---|---|---|---|---|---|---|
| | | | 100 | | | | | 105 | | | | | 110 | | |

| Thr | Ser | Thr | Lys | Val | Lys | Glu | Glu | Ser | Lys | Thr | Gln | Ser | Asp | Ser | Gln |
|---|---|---|---|---|---|---|---|---|---|---|---|---|---|---|---|
| | | 115 | | | | | 120 | | | | | 125 | | | |

| Ala | Ser | Val | Lys | Ser | Glu | Thr | Pro | Glu | Glu | Asp | Gln | Gly | Tyr | Lys | Trp |
|---|---|---|---|---|---|---|---|---|---|---|---|---|---|---|---|
| | 130 | | | | | 135 | | | | | 140 | | | | |

| Trp | Glu | Val | Asn | Gln | Glu | Glu | Gly | Asp | Gly | Tyr | Ile | Lys | Trp | Gln |
|---|---|---|---|---|---|---|---|---|---|---|---|---|---|---|
| 145 | | | | | 150 | | | | | 155 | | | | 160 |

| Thr | Leu | Glu | His | Asn | Gly | Val | Met | Phe | Pro | Pro | Tyr | Glu | Pro | Leu |
|---|---|---|---|---|---|---|---|---|---|---|---|---|---|---|
| | | | | 165 | | | | | 170 | | | | | 175 |

| Pro | Ser | His | Val | Lys | Leu | Tyr | Tyr | Asn | Asn | Lys | Pro | Val | Asn | Leu | Pro |
|---|---|---|---|---|---|---|---|---|---|---|---|---|---|---|---|
| | | | 180 | | | | | 185 | | | | | 190 | | |

| Pro | Glu | Ala | Glu | Glu | Val | Ala | Gly | Phe | Tyr | Gly | Ala | Met | Leu | Glu | Thr |
|---|---|---|---|---|---|---|---|---|---|---|---|---|---|---|---|
| | | 195 | | | | | 200 | | | | | 205 | | | |

| Asp | His | Ala | Lys | Asn | Pro | Val | Phe | Gln | Lys | Asn | Phe | Phe | Asn | Asp | Phe |
|---|---|---|---|---|---|---|---|---|---|---|---|---|---|---|---|
| | 210 | | | | | 215 | | | | | 220 | | | | |

| Leu | Glu | Val | Leu | Lys | Glu | Cys | Gly | Gly | Cys | Gly | Val | Glu | Ile | Lys | Lys |
|---|---|---|---|---|---|---|---|---|---|---|---|---|---|---|---|
| 225 | | | | | 230 | | | | | 235 | | | | | 240 |

| Phe | Glu | Lys | Leu | Asp | Phe | Ser | Lys | Met | Tyr | Ala | His | Phe | Glu | Lys | Leu |
|---|---|---|---|---|---|---|---|---|---|---|---|---|---|---|---|
| | | | | 245 | | | | | 250 | | | | | 255 | |

| Arg | Glu | Glu | Lys | Lys | Ala | Met | Ser | Arg | Glu | Glu | Lys | Lys | Arg | Ile | Lys |
|---|---|---|---|---|---|---|---|---|---|---|---|---|---|---|---|
| | | | 260 | | | | | 265 | | | | | 270 | | |

| Glu | Glu | Lys | Glu | Lys | Glu | Glu | Glu | Pro | Tyr | Arg | Thr | Cys | Tyr | Leu | Asn |
|---|---|---|---|---|---|---|---|---|---|---|---|---|---|---|---|
| | | 275 | | | | | 280 | | | | | 285 | | | |

| Gly | Arg | Lys | Glu | Leu | Val | Gly | Asn | Phe | Arg | Ile | Glu | Pro | Pro | Gly | Leu |
|---|---|---|---|---|---|---|---|---|---|---|---|---|---|---|---|
| | 290 | | | | | 295 | | | | | 300 | | | | |

| Phe | Arg | Gly | Arg | Gly | Ala | His | Pro | Lys | Thr | Gly | Lys | Leu | Lys | Arg | Arg |
|---|---|---|---|---|---|---|---|---|---|---|---|---|---|---|---|
| 305 | | | | | 310 | | | | | 315 | | | | | 320 |

| Val | Val | Leu | Glu | Gln | Val | Thr | Leu | Asn | Leu | Gly | Lys | Asp | Ala | Lys | Ile |
|---|---|---|---|---|---|---|---|---|---|---|---|---|---|---|---|
| | | | | 325 | | | | | 330 | | | | | 335 | |

| Pro | Glu | Pro | Pro | Ala | Gly | His | Gln | Trp | Gly | Glu | Ile | Arg | His | Asp | Asn |
|---|---|---|---|---|---|---|---|---|---|---|---|---|---|---|---|
| | | | 340 | | | | | 345 | | | | | 350 | | |

| Glu | Val | Thr | Trp | Leu | Ala | Met | Trp | Lys | Glu | Asn | Ile | Ser | Asp | Ser | Leu |
|---|---|---|---|---|---|---|---|---|---|---|---|---|---|---|---|
| | | 355 | | | | | 360 | | | | | 365 | | | |

| Lys | Tyr | Val | Arg | Phe | Ala | Asn | Asn | Ser | Ser | Val | Lys | Gly | Gln | Ser | Asp |
|---|---|---|---|---|---|---|---|---|---|---|---|---|---|---|---|
| | 370 | | | | | 375 | | | | | 380 | | | | |

| Phe | Lys | Lys | Phe | Glu | Thr | Ala | Arg | Lys | Leu | Arg | Asp | His | Val | Asp | Ser |
|---|---|---|---|---|---|---|---|---|---|---|---|---|---|---|---|
| 385 | | | | | 390 | | | | | 395 | | | | | 400 |

| Ile | Arg | Lys | Asp | Tyr | Thr | Lys | Met | Leu | Lys | Ser | Glu | Lys | Met | Gln | Asp |
|---|---|---|---|---|---|---|---|---|---|---|---|---|---|---|---|
| | | | | 405 | | | | | 410 | | | | | 415 | |

-continued

```
Arg  Gln  Met  Ala  Thr  Ala  Met  Tyr  Leu  Ile  Asp  Val  Phe  Ala  Leu  Arg
               420                 425                      430

Ala  Gly  Gly  Glu  Lys  Gly  Glu  Asp  Glu  Ala  Asp  Thr  Val  Gly  Cys  Cys
          435                      440                      445

Ser  Leu  Arg  Tyr  Glu  His  Val  Thr  Leu  Lys  Pro  Pro  Asn  Lys  Val  Ile
     450                      455                 460

Phe  Asp  Phe  Leu  Gly  Lys  Asp  Ser  Ile  Arg  Phe  Tyr  Gln  Glu  Val  Glu
465                      470                 475                           480

Val  Asp  Lys  Gln  Val  Phe  Lys  Asn  Leu  Arg  Ile  Phe  Lys  Lys  Ser  Pro
               485                           490                      495

Lys  Gln  Pro  Gly  Asp  Asp  Leu  Phe  Asp  Arg  Ile  Asn  Pro  Ser  Leu  Val
               500                 505                      510

Asn  Arg  Gln  Leu  Gln  Asn  Tyr  Met  Lys  Gly  Leu  Thr  Ala  Lys  Val  Phe
          515                      520                      525

Arg  Thr  Tyr  Asn  Ala  Ser  Lys  Thr  Met  Gln  Asp  Gln  Ile  Asp  Ile  Ile
     530                      535                      540

Glu  Asn  Glu  Gly  Thr  Val  Ala  Glu  Lys  Val  Ala  Lys  Phe  Asn  Ala  Ala
545                      550                      555                      560

Asn  Arg  Thr  Val  Ala  Ile  Leu  Cys  Asn  His  Gln  Arg  Thr  Val  Ser  Lys
               565                      570                      575

Thr  His  Gly  Asp  Ser  Val  Gln  Arg  Ile  Asn  Asp  Lys  Leu  Lys  Lys  Phe
               580                      585                      590

Met  Trp  Gln  Lys  Ile  Arg  Leu  Lys  Lys  Met  Ile  Leu  Gln  Leu  Glu  Pro
          595                      600                      605

Lys  Leu  Lys  Lys  Lys  Asp  Ser  Lys  Tyr  Phe  Glu  Glu  Ile  Asp  Asp  Leu
     610                      615                 620

Leu  Lys  Glu  Asp  Ile  Glu  His  Ile  His  His  Thr  Ile  Ile  Lys  Arg  Gln
625                      630                 635                           640

Arg  Glu  Gln  Ala  Lys  Lys  Leu  Glu  Arg  Asp  Asn  Glu  Lys  Leu  Lys
                    645                      650                      655

Leu  Glu  Gly  Lys  Pro  Leu  Leu  Thr  Glu  Ser  Asp  Ile  Lys  Asp  Lys  Leu
               660                      665                      670

Asp  Lys  Ile  Asp  Glu  Leu  Glu  Lys  Glu  Tyr  Gln  Lys  Glu  Leu  Lys  Thr
          675                      680                      685

Gly  Lys  Pro  Ile  Val  Thr  Lys  Asn  Ala  Thr  Val  Glu  Lys  Leu  Lys  Gln
     690                      695                 700

Gln  Ile  Glu  Thr  Leu  Glu  Asn  Lys  Ile  Leu  Asn  Val  Ser  Ile  Gln  Leu
705                      710                 715                           720

Lys  Asp  Lys  Glu  Asp  Asn  Ser  Glu  Val  Ser  Leu  Gly  Thr  Ser  Lys  Met
               725                      730                      735

Asn  Tyr  Ile  Asp  Pro  Arg  Leu  Ile  Val  Met  Phe  Ser  Lys  Lys  Phe  Asp
               740                      745                      750

Val  Pro  Ile  Glu  Lys  Leu  Phe  Thr  Lys  Thr  Leu  Arg  Glu  Lys  Phe  Ile
          755                      760                      765

Trp  Ala  Ile  Glu  Ser  Ala  Asp  Glu  Asn  Trp  Arg  Phe
     770                 775                      780
```

ANTI-FUNGAL AGENTS AND METHODS OF IDENTIFYING AND USING THE SAME

FIELD OF THE INVENTION

The invention relates to the identification and cloning of the topoisomerase I gene (TOP1) from *Candida albicans* and the use of the gene in complementation assays to identify inhibitors of the *C. albicans* TOP1 while having no effect on the homologous human TOP1. The invention relates to compounds that selectively inhibit *C. albicans* TOP1 and the use of such compounds to kill fungi and in the treatment of individuals with fungal infections.

BACKGROUND OF THE INVENTION

*Candida albicans* is the most important fungal pathogen infecting humans. This fungal pathogen causes vaginal yeast infections, as well as oral infections and tissue invasion in immunocompromised patients. Oral infections are highly prevalent in AIDS patients and in cancer patients undergoing bone marrow replacement therapy. Only three types of anti-fungal drugs are currently approved for use in humans. Unfortunately, these anti-fungal drugs have serious side effects and have limited efficacy.

There is a need for compounds which selectively inhibit *C. albicans* topoisomerase I activity but which do not inhibit human topoisomerase I activity. There is a need for kits and methods of identifying such compounds. There is a need for isolated *C. albicans* topoisomerase I protein, and for compositions and methods of producing and isolating *C. albicans* topoisomerase I protein.

SUMMARY OF THE INVENTION

The present invention relates to substantially pure *C. albicans* topoisomerase I protein.

The present invention relates to substantially pure *C. albicans* topoisomerase I protein having the amino acid sequence of SEQ ID NO:2.

The present invention relates to nucleic acid molecules that encode *C. albicans* topoisomerase I protein.

The present invention relates to nucleic acid molecules encoding *C. albicans* topoisomerase I protein that consists of SEQ ID NO:1.

The present invention relates to recombinant expression vectors that comprise a nucleic acid sequence that encodes *C. albicans* topoisomerase I protein.

The present invention relates to host cells that comprise recombinant expression vectors that encode *C. albicans* topoisomerase I protein.

The present invention relates to fragments of nucleic acid molecules with sequences encoding *C. albicans* topoisomerase I protein that have at least 10 nucleotides.

The present invention relates to oligonucleotide molecules that comprise a nucleotide sequence complimentary to a nucleotide sequence of at least 10 nucleotides of SEQ ID NO:1.

The present invention relates to isolated antibodies which bind to an epitope on SEQ ID NO:2.

The present invention relates to host cells that have deficient or non-functional endogenous topoisomerase I proteins and comprise recombinant expression vectors that encode *C. albicans* topoisomerase I protein.

The present invention relates to methods of identifying inhibitors of *C. albicans* topoisomerase I protein. The methods comprise contacting a first host cell which is deficient in a functional topoisomerase gene except for a functional gene that encodes *C. albicans* topoisomerase I protein with a test compound, contacting a second host cell which is deficient in a functional topoisomerase gene except for a functional gene that encodes non-*C. albicans* topoisomerase I protein with a test compound, and identifying a test compound whose presence results in the death of the first host cell but not the second host cell.

DETAILED DESCRIPTION OF THE INVENTION

The present invention provides the cloned gene that encodes *C. albicans* topoisomerase I protein. The discovery of the *C. albicans* topoisomerase I gene and the protein that it encodes provides the means to design and discover specific inhibitors of *C. albicans* topoisomerase I protein. As used herein the terms "specific inhibitor of *C. albicans* topoisomerase I protein" and "selective inhibitor of *C. albicans* topoisomerase I protein" are used interchangeably and are meant to refer to compounds that result in the death of *C. albicans* through the inhibition of activity of *C. albicans* topoisomerase I protein but that do not kill non-*C. albicans* species which come into contact with the compound. Compounds that selectively inhibit *C. albicans* topoisomerase I activity are those which inhibit *C. albicans* topoisomerase I activity but not the activity of non-*C. albicans* topoisomerase I proteins.

According to the present invention, the gene that encodes *C. albicans* topoisomerase I protein may be used to produce recombinant microorganisms that are useful to screen compounds for specific inhibitors. A host organism deficient in endogenous topoisomerase I protein may be "complemented" with *C. albicans* topoisomerase I, i.e. furnished with a functional copy of the *C. albicans* topoisomerase I gene or cDNA. Expression of the nucleotide sequence that encodes *C. albicans* topoisomerase I protein results in production of functional protein which functions in place of the missing or non-functional endogenous topoisomerase I. Comparative studies can be performed to evaluate the effect test compounds have on the hosts that are complemented with *C. albicans* topoisomerase I compared to the effect the same test compounds have on the hosts with functional endogenous topoisomerase I or hosts that are complemented with non-*C. albicans* topoisomerase I. In some preferred embodiments, inhibitors are identified using complementation assays in which a first host cell that expresses *C. albicans* topoisomerase I protein to survive is contacted with a test compound and a second host cell which expresses a non-*C. albicans* topoisomerase I protein to survive is contacted with the same test compound. If the first host cell dies in the presence of the test compound but the second host cell lives in the presence of the same test compound, the compound is indicated to be an inhibitor of *C. albicans* topoisomerase I protein.

Complemented host cells are deficient for functional endogenous topoisomerase I and rely on the activity of "foreign" topoisomerase I for survival. Host cells that are deficient for functional endogenous topoisomerase I and which can be complemented by "foreign" topoisomerase I for survival include yeasts, *Saccharomyces species*, *Schizosaccharomyces species*, *Escherichia coli*, and *Salmonella typhimurium*. In some preferred embodiments, complemented host cells are yeasts. In some preferred embodiments, complemented host cells are yeast strain L1242, which is described in Thrash, et al., *Proc. Natl. Acad. Sci. USA*, 1985, 82, 4374–4378, which is disclosed in its entirety herein by reference, or other top1⁻ yeast strains.

Expression of human TOP1 in yeast is described in Bjornsti, et al., *Cancer Res.*, 1989, 49, 6318–6323, which is disclosed in its entirety herein by reference. Bjornsti, et al., describe the complementation of conditional lethal human topoisomerase I mutant. In a similar manner, yeasts and the like can be transformed with nucleic acid molecules encoding *C. albicans* topoisomerase I protein that consists of SEQ ID NO:2. Accordingly, complementation can be performed with yeasts transformed with nucleic acid molecules encoding *C. albicans* topoisomerase I protein that consists of SEQ ID NO:2.

The methods of the invention are useful to identify selective inhibitors of *C. albicans* topoisomerase I protein. Inhibitors are useful as anti-fungal agents, specifically anti-*C. albicans* agents. Kits are provided for screening compounds for identifying selective inhibitors of *C. albicans* topoisomerase I protein.

The nucleotide sequence that encodes *C. albicans* topoisomerase I protein and that is disclosed herein as SEQ ID NO:1 allows for the production of complemented host cells which survive due to the presence of functional *C. albicans* topoisomerase I protein. In preparing gene constructs for complementation of deficient hosts, SEQ ID NO:1 is introduced into a host and expressed. SEQ ID NO:1 may be inserted into an expression vector in which the coding sequence is operably linked to regulatory elements required for gene expression in the host. In some preferred embodiments the expression vector is pBM272, which allows regulated expression from the GAL1 promoter of *Saccharomyces cerevisiae*. The wild-type *C. albicans* TOP1 coding sequence can be inserted into the BamHI and HindIII sites of pBM272. As controls, deficient host cells may be complemented with human topoisomerase I or another topoisomerase I.

The nucleotide sequence that encodes *C. albicans* topoisomerase I protein and that is disclosed herein as SEQ ID NO:1 allows for the production of pure *C. albicans* topoisomerase I protein and the design of probes which specifically hybridize to nucleic acid molecules that encode *C. albicans* topoisomerase I protein and antisense compounds to inhibit transcription of the gene that encodes *C. albicans* topoisomerase I protein.

The present invention provides substantially purified *C. albicans* topoisomerase I protein. The present invention provides substantially purified *C. albicans* topoisomerase I protein which has the amino acid sequence consisting of SEQ ID NO:2. *C. albicans* topoisomerase I protein can be isolated from natural sources or produced by recombinant DNA methods.

The *C. albicans* topoisomerase I protein sequence differs substantially from the human topoisomerase I sequence. Such differences may be used to predict which compounds might show specific binding or inhibition of the *C. albicans* topoisomerase I. In particular, the active site region of the *C. albicans* topoisomerase I has a methionine residue, Met736, instead of the leucine/isoleucine located 2 residues amino-terminal to the active site tyrosine, Tyr738, found in human and other eukaryotic topoisomerase I proteins. Antibodies may be generated and selected which specifically bind to *C. albicans* topoisomerase I at an epitope which includes the methionine within the active site.

Antibodies that specifically bind to *C. albicans* topoisomerase I protein are provided. Such antibodies are specific inhibitors of *C. albicans* topoisomerase I protein and may be used in methods of isolating pure *C. albicans* topoisomerase I protein and methods of inhibiting *C. albicans* topoisomerase I protein activity.

The antibodies may be used to purify the protein from natural sources using well known techniques and readily available starting materials. Such antibodies may also be used to purify *C. albicans* topoisomerase I protein from material present when producing the protein by recombinant DNA methodology. The present invention relates to antibodies that bind to an epitope which is specific for *C. albicans* topoisomerase I protein as compared to human topoisomerase I protein. This epitope appears at amino acids 730 to 740 of SEQ ID NO:2.

As used herein, the term "antibody" is meant to refer to complete, intact antibodies, and Fab fragments and F(ab)$_2$ fragments thereof. Complete, intact antibodies include monoclonal antibodies such as murine monoclonal antibodies, chimeric antibodies and humanized antibodies. The antibodies specifically bind to an epitope on SEQ ID NO:2. In some preferred embodiments, that epitope appears at amino acids 730 to 740 of SEQ ID NO:2. Antibodies that bind to an epitope on SEQ ID NO:2, particularly at amino acids 730 to 740 of SEQ ID NO:2 are useful to isolate and purify *C. albicans* topoisomerase I protein from both natural sources or recombinant expression systems using well known techniques such as affinity chromatography. Such antibodies are useful to detect the presence of such protein in a sample and to determine if cells are expressing the protein.

The production of antibodies and the protein structures of complete, intact antibodies, Fab fragments and F(ab)$_2$ fragments and the organization of the genetic sequences that encode such molecules are well known and are described, for example, in Harlow, E. and D. Lane (1988) *ANTIBODIES: A Laboratory Manual*, Cold Spring Harbor Laboratory, Cold Spring Harbor, N.Y., which is incorporated herein by reference. Briefly, for example, the *C. albicans* topoisomerase I protein, or an immunogenic fragment thereof is injected into mice. The spleen of the mouse is removed, the spleen cells are isolated and fused with immortalized mouse cells. The hybrid cells, or hybridomas, are cultured and those cells which secrete antibodies are selected. The antibodies are analyzed and, if found to specifically bind to *C. albicans* topoisomerase I protein, the hybridoma which produces them is cultured to produce a continuous supply of antibodies.

Using standard techniques and readily available starting materials, a nucleic acid molecule that encodes *C. albicans* topoisomerase I protein may be isolated from a cDNA library, using probes which are designed using the nucleotide sequence information disclosed in SEQ ID NO:1. The present invention relates to an isolated nucleic acid molecule that comprises a nucleotide sequence that encodes *C. albicans* topoisomerase I protein and that comprises the amino acid sequence of SEQ ID NO:2. In some embodiments, the nucleic acid molecules consist of a nucleotide sequence that encodes *C. albicans* topoisomerase I protein. In some embodiments, the nucleic acid molecules comprise the nucleotide sequence that consists of the coding sequence in SEQ ID NO:1. In some embodiments, the nucleic acid molecules consist of the nucleotide sequence set forth in SEQ ID NO:1. The isolated nucleic acid molecules of the invention are useful to prepare constructs and recombinant expression systems for preparing isolated *C. albicans* topoisomerase I protein.

A genomic or cDNA library may be generated by well known techniques. Clones are identified using probes that comprise at least a portion of the nucleotide sequence disclosed in SEQ ID NO:1. The probes have at least 16 nucleotides, preferably 24 nucleotides. The probes are used to screen the genomic or cDNA libraries using standard hybridization techniques. In addition, the probes of the invention may be used to identify topoisomerase I genes from related organisms such as *Aspergillus fumigatus* and *Cryptosporidium species*.

The present invention relates to isolated nucleic acid molecules that comprise a nucleotide sequence identical or complementary to a fragment of SEQ ID NO:1 which is at least 10 nucleotides. In some embodiments, the isolated nucleic acid molecules consist of a nucleotide sequence identical or complementary to a fragment of SEQ ID NO:1 which is at least 10 nucleotides. In some embodiments, the isolated nucleic acid molecules comprise or consist of a nucleotide sequence identical or complementary to a fragment of SEQ ID NO:1 which is 15–150 nucleotides. In some embodiments, the isolated nucleic acid molecules comprise or consist of a nucleotide sequence identical or complementary to a fragment of SEQ ID NO:1 which is 15–30 nucleotides.

Isolated nucleic acid molecules that comprise or consist of a nucleotide sequence identical or complementary to a fragment of SEQ ID NO:1 which is at least 10 nucleotides are useful as probes for identifying genes and cDNA sequences that encodes *C. albicans* topoisomerase I protein, PCR primers for amplifying genes and cDNA that encodes *C. albicans* topoisomerase I protein, and antisense molecules for inhibiting transcription and translation of genes and cDNA, respectively, which encode *C. albicans* topoisomerase I protein.

The nucleotide sequence in SEQ ID NO:1 may be used to design probes, primers and complimentary molecules which specifically hybridize to the unique nucleotide sequences of *C. albicans* topoisomerase I protein. Probes, primers and complimentary molecules which specifically hybridize to nucleotide sequence that encodes *C. albicans* topoisomerase I protein may be designed routinely by those having ordinary skill in the art.

The present invention also includes labelled oligonucleotides which are useful as probes for performing oligonucleotide hybridization methods to identify clones that encode *C. albicans* topoisomerase I protein. Accordingly, the present invention includes probes that can be labelled and hybridized to unique nucleotide sequences of nucleic acid molecules that encode *C. albicans* topoisomerase I protein. The labelled probes of the present invention are labelled with radiolabelled nucleotides or are otherwise detectable by readily available nonradioactive detection systems. In some preferred embodiments, probes comprise oligonucleotides consisting of between 10 and 100 nucleotides. In some preferred, probes comprise oligonucleotides consisting of between 10 and 50 nucleotides. In some preferred, probes comprise oligonucleotides consisting of between 12 and 20 nucleotides. The probes preferably contain nucleotide sequence completely identical or complementary to a fragment of a unique nucleotide sequences of nucleic acid molecules that encode *C. albicans* topoisomerase I protein.

PCR technology is practiced routinely by those having ordinary skill in the art and its uses in diagnostics are well known and accepted. Methods for practicing PCR technology are disclosed in "PCR Protocols: A Guide to Methods and Applications", Innis, M. A., et al. Eds. Academic Press, Inc. San Diego, Calif. (1990), which is incorporated herein by reference. Applications of PCR technology are disclosed in "Polymerase Chain Reaction" Erlich, H. A., et al., Eds. Cold Spring Harbor Press, Cold Spring Harbor, N.Y. (1989), which is incorporated herein by reference. Some simple rules aid in the design of efficient primers. Typical primers are 18–28 nucleotides in length having 50% to 60% g+c composition. The entire primer is preferably complementary to the sequence it must hybridize to. Preferably, primers generate PCR products 100 basepairs to 2000 base pairs. However, it is possible to generate products of 50 base pairs to up to 10 kb and more.

PCR technology allows for the rapid generation of multiple copies of nucleotide sequences by providing 5' and 3' primers that hybridize to sequences present in a nucleic acid molecule, and further providing free nucleotides and an enzyme which fills in the complementary bases to the nucleotide sequence between the primers with the free nucleotides to produce a complementary strand of DNA. The enzyme will fill in the complementary sequences adjacent to the primers. If both the 5' primer and 3' primer hybridize to nucleotide sequences on the complementary strands of the same fragment of nucleic acid, exponential amplification of a specific double-stranded product results. If only a single primer hybridizes to the nucleic acid molecule, linear amplification produces single-stranded products of variable length.

One having ordinary skill in the art can isolate the nucleic acid molecule that encodes *C. albicans* topoisomerase I protein and insert it into an expression vector using standard techniques and readily available starting materials.

The present invention relates to a recombinant expression vector that comprises a nucleotide sequence that encodes *C. albicans* topoisomerase I protein that comprises the amino acid sequence of SEQ ID NO:2. As used herein, the term "recombinant expression vector" is meant to refer to a plasmid, phage, viral particle or other vector which, when introduced into an appropriate host, contains the necessary genetic elements to direct expression of the coding sequence that encodes the *C. albicans* topoisomerase I protein. The coding sequence is operably linked to the necessary regulatory sequences. Expression vectors are well known and readily available. Examples of expression vectors include plasmids, phages, viral vectors and other nucleic acid molecules or nucleic acid molecule containing vehicles useful to transform host cells and facilitate expression of coding sequences. In some embodiments, the recombinant expression vector comprises the nucleotide sequence set forth in SEQ ID NO:1. The recombinant expression vectors of the invention are useful for transforming hosts to prepare recombinant expression systems for preparing the *C. albicans* topoisomerase I protein.

The present invention relates to a host cell that comprises the recombinant expression vector that includes a nucleotide sequence that encodes *C. albicans* topoisomerase I protein that comprises SEQ ID NO:2. In some embodiments, the host cell comprises a recombinant expression vector that comprises SEQ ID NO:1. Host cells for use in well known recombinant expression systems for production of proteins are well known and readily available. Examples of host cells include bacteria cells such as *E. coli*, yeast cells such as *S. cerevisiae*, insect cells such as *S. frugiperda*, non-human mammalian tissue culture cells chinese hamster ovary (CHO) cells and human tissue culture cells such as HeLa cells.

The present invention relates to a transgenic, non-human mammal that comprises the recombinant expression vector that comprises a nucleic acid sequence that encodes the *C. albicans* topoisomerase I protein that comprises the amino acid sequence of SEQ ID NO:2. Transgenic, non-human mammals useful to produce recombinant proteins are well known as are the expression vectors necessary and the techniques for generating transgenic animals. Generally, the transgenic animal comprises a recombinant expression vector in which the nucleotide sequence that encodes *C. albicans* topoisomerase I protein operably linked to a mammary cell specific promoter whereby the coding sequence is only expressed in mammary cells and the recombinant protein so expressed is recovered from the animal's milk. In some embodiments, the coding sequence that encodes *C. albicans* topoisomerase 1 protein is SEQ ID NO:1.

In some embodiments, for example, one having ordinary skill in the art can, using well known techniques, insert such DNA molecules into a commercially available expression vector for use in well known expression systems. For example, the commercially available plasmid pSE420 (Invitrogen, San Diego, Calif.) may be used for production of *C. albicans* topoisomerase I in *E. coli*. The commercially available plasmid pYES2 (Invitrogen, San Diego, Calif.) may, for example, be used for production in *S. cerevisiae* strains of yeast. The commercially available MAXBAC™ complete baculovirus expression system (Invitrogen, San Diego, Calif.) may, for example, be used for production in insect cells. The commercially available plasmid pcDNA I (Invitrogen, San Diego, Calif.) may, for example, be used for production in mammalian cells such as CHO cells. One having ordinary skill in the art can use these commercial expression vectors and systems or others to produce *C. albicans* topoisomerase I protein using routine techniques and readily available starting materials. (See e.g., Sambrook et al., *Molecular Cloning a Laboratory Manual*, Second Ed. Cold Spring Harbor Press (1989), which is incorporated herein by reference.) Thus, the desired proteins can be prepared in both prokaryotic and eukaryotic systems, resulting in a spectrum of processed forms of the protein.

One having ordinary skill in the art may use other commercially available expression vectors and systems or produce vectors using well known methods and readily available starting materials. Expression systems containing the requisite control sequences, such as promoters and polyadenylation signals, and preferably enhancers, are readily available and known in the art for a variety of hosts. See e.g., Sambrook et al., *Molecular Cloning a Laboratory Manual*, Second Ed. Cold Spring Harbor Press (1989).

A wide variety of eukaryotic hosts are also now available for production of recombinant foreign proteins. As in bacteria, eukaryotic hosts may be transformed with expression systems which produce the desired protein directly, but more commonly signal sequences are provided to effect the secretion of the protein. Eukaryotic systems have the additional advantage that they are able to process introns which may occur in the genomic sequences encoding proteins of higher organisms. Eukaryotic systems also provide a variety of processing mechanisms which result in, for example, glycosylation, carboxy-terminal amidation, oxidation or derivatization of certain amino acid residues, conformational control, and so forth.

Commonly used eukaryotic systems include, but is not limited to, yeast, fungal cells, insect cells, mammalian cells, arian cells, and cells of higher plants. Suitable promoters are available which are compatible and operable for use in each of these host types as well as are termination sequences and enhancers, e.g. the baculovirus polyhedron promoter. As above, promoters can be either constitutive or inducible. For example, in mammalian systems, the mouse metallothionein promoter can be induced by the addition of heavy metal ions.

The particulars for the construction of expression systems suitable for desired hosts are known to those in the art. Briefly, for recombinant production of the protein, the DNA encoding the polypeptide is suitably ligated into the expression vector of choice. The DNA is operably linked to all regulatory elements which are necessary for expression of the DNA in the selected host. One having ordinary skill in the art can, using well known techniques, prepare expression vectors for recombinant production of the polypeptide.

The expression vector including the DNA that encodes *C. albicans* topoisomerase I protein is used to transform the compatible host which is then cultured and maintained under conditions wherein expression of the foreign DNA takes place. The protein of the present invention thus produced is recovered from the culture, either by lysing the cells or from the culture medium as appropriate and known to those in the art. One having ordinary skill in the art can, using well known techniques, isolate *C. albicans* topoisomerase I protein that is produced using such expression systems. The methods of purifying *C. albicans* topoisomerase I protein from natural sources using antibodies which specifically bind to *C. albicans* topoisomerase I protein as described above, may be equally applied to purifying *C. albicans* topoisomerase I protein produced by recombinant DNA methodology.

Examples of genetic constructs include the *C. albicans* topoisomerase I protein coding sequence operably linked to a promoter that is functional in the cell line into which the constructs are transfected. Examples of constitutive promoters include promoters from cytomegalovirus or SV40. Examples of inducible promoters include mouse mammary leukemia virus or metallothionein promoters. Those having ordinary skill in the art can readily produce genetic constructs useful for transfecting with cells with DNA that encodes *C. albicans* topoisomerase I protein from readily available starting materials. Such gene constructs are useful for the production of *C. albicans* topoisomerase I protein.

In some embodiments of the invention, transgenic non-human animals are generated. The transgenic animals according to the invention contain SEQ ID NO:1 under the regulatory control of a mammary specific promoter. One having ordinary skill in the art using standard techniques, such as those taught in U.S. Pat. No. 4,873,191 issued Oct. 10, 1989 to Wagner and U.S. Pat. No. 4,736,866 issued Apr. 12, 1988 to Leder, both of which are incorporated herein by reference, can produce transgenic animals which produce the *C. albicans* topoisomerase I protein. Preferred animals are rodents, particularly goats, rats and mice.

In addition to producing these proteins by recombinant techniques, automated peptide synthesizers may also be employed to produce *C. albicans* topoisomerase I protein. Such techniques are well known to those having ordinary skill in the art and are useful if derivatives which have substitutions not provided for in DNA-encoded protein production.

To screen compounds according to the methods of the present invention, at least two groups of host cells are tested. One host cell is complemented with functional *C. albicans* topoisomerase I. The other host cell either contains a functional endogenous topoisomerase I or is complemented with a non-*C. albicans* topoisomerase, preferably human topoisomerase. The groups are contacted with test compounds and the survivability of each of the two groups is observed. If a test compound leads to the death of the host cells complemented with *C. albicans* topoisomerase I but not those with non-*C. albicans* topoisomerase I, the compound is a selective inhibitor of *C. albicans* topoisomerase I.

In some embodiments of the invention, the preferred concentration of test compound is between 1 μM and 500 μM. A preferred concentration is 10 μM to 100 μM. In some preferred embodiments, it is desirable to use a series of dilutions of test compounds.

Kits are included which comprise containers with host cells or reagents necessary to produce host cells and/or screen test compounds. In additions, kits comprise instructions for performing such methods.

EXAMPLES

Example 1

The topoisomerase I gene (TOP1) from *Candida albicans* is highly expressed in a yeast (*Saccharomyces cerevisiae*) strain lacking its native yeast TOP1 gene. The human TOP1 gene is highly expressed in a second top1-yeast strain. These two yeast strains are used to screen chemical compounds to find compounds which kill or inhibit the yeast expressing *C. albicans* TOP1 but not the yeast expressing the human TOP1.

*C. albicans* TOP1 was cloned using PCR. The PCR fragment was used as a probe to select a full-length TOP1 clone. The DNA sequence of the *C. albicans* TOP1 gene was determined and used to predict the topoisomerase I peptide sequence. The gene was excised from the DNA library vector using restriction enzymes, modified at the start of the protein-coding sequence, and ligated into a yeast expression plasmid. This plasmid is transformed into a top1$^-$ yeast strain.

The *C. albicans* topoisomerase I protein sequence differs substantially from the human topoisomerase I sequence. Such differences may be used to predict which compounds might show specific binding or inhibition of the *C. albicans* topoisomerase I. In particular, the active site region has a methionine residue in place of the usual leucine/isoleucine located 2 residues amino-terminal to the active site tyrosine. Drugs may be selected based on ability to interact with this methionine residue.

It has been shown previously that overexpression of a TOP1 gene from another organism sensitizes a host yeast strain to camptothecin. Camptothecin kills such yeast strains by stabilizing a covalent topoisomerase I-DNA conjugate which leaves a broken DNA strand. The broken single strand can be processed to a double-strand break during DNA replication. If this damage is not repaired by DNA recombination, it leads to cell death.

The fastest ways to screen chemical or natural extracts from activity against *C. albicans* topoisomerase I is an adaption of the "zone of inhibition" assay for antibiotics. Two yeast strains, one expressing *C. albicans* topoisomerase I and the other strain expressing human topoisomerase I, are spread into a lawn of cells on minimal medium in 2 petri-dishes. Duplicate small paper discs are soaked in solutions of chemicals or natural products, and transferred to the surfaces of each of the 2 petri dishes. After 2–4 days at 30°, a thick lawn of yeast cells will grow on the petri-dishes. A compound which produces a clear "zone of inhibition" of growth on the *C. albicans* TOP1 dish, but not the human TOP1 dish, is a specific inhibitor of *C. albicans* topoisomerase I.

In another embodiment of the assay, the two yeast strains, one expressing *C. albicans* topoisomerase I and the other expressing human topoisomerase I, are grown in liquid medium containing a possible inhibitory agent. A compound that inhibits the growth of *C. albicans* TOP1 yeast strain, but not the human TOP1 yeast strain, is a specific inhibitor of the *C. albicans* topoisomerase I.

Example 2

Yeast Transformation

The plasmid pBM-CaTOP1, and a similar plasmid expressing the human TOP1 gene, can be transformed into a top1$^-$ *S. cerevisiae* strain by standard techniques, such as those described in Elble, R., *Biotechniques*, 1992, 13(1), 78–80, which is disclosed in its entirety herein by reference. The plasmid can be selected by growing the yeast strain in minimal medium lacking uracil. The URA3 gene within pBM-CaTOP1 will enable the yeast strain to grow on medium lacking uracil. The expression of *C. albicans* topoisomerase I in *S. cerevisiae* can be verified by assaying the ability of a crude extract of this yeast strain to remove plasmid DNA supercoils as detailed in Thrash, et al., *Proc. Natl. Acad. Sci. USA*, 1985, 82, 4374–4378, which is disclosed in its entirety herein by reference.

Cloning *C. albicans* TOP1 Gene Into Expression Vector pBM272

The native genomic *C. albicans* TOP1 clone pCaT1-R12 constitutes a 3.4 kb EcoRI-EcoRI fragment containing the entire TOP1 gene, ligated into the pBC SK(-) plasmid (Stratagene, La Jolla, Calif.). This gene was modified by introducing a BamHI restriction site immediately 5' upstream of the coding sequence using standard techniques (Sambrook, et al., *Molecular Cloning a Laboratory Manual*, Second Ed. Cold Spring Harbor Press (1989)). The entire gene coding sequence was excised as a 2.4 kb BamHI-HindIII DNA fragment, and ligated into the BamHI-HindIII sites of yeast expression vector pBM272 using standard techniques. This plasmid, pBM-CaTOP1, can be introduced into top1$^-$ yeast strain L1242 (*S. cerevisiae;* Thrash, et al., *Proc. Natl. Acad. Sci. USA*, 1985, 82, 4374–4378) or a derivative strain, K2979, provided by Dr. Ralph Keil, Hershey Medical Center, Hershey, Pa.). The K2979 genotype is: MATa HindIII(top1::LEU2) his4-260 ade2-1 ura3-52 leu2-3,112 trp1-HIII can1$^R$ lys2ΔBX::CAN1::LYS2 rDN-A::URA3 rDNA::ADE2.

The cloned genomic *C. albicans* TOP1 gene can also be used to generate a top1$^-$/top1$^-$ *C. albicans* strain using the gene for gene disruption using standard techniques known to fungal geneticists.

---

We claim:

1. A recombinant expression vector comprising a nucleic acid sequence that encodes the protein of SEQ ID NO:2.

2. A host cell comprising the recombinant expression vector of claim 1.

3. An isolated nucleic acid molecule consisting of SEQ ID NO:1.

4. A recombinant expression vector comprising the nucleic acid molecule of claim 3.

5. A host cell comprising the recombinant expression vector of claim 4.

6. The host cell of claim 5 wherein said host cell is deficient in and/or contains non-functional endogenous topoisomerase I protein.

7. The host cell of claim 6 wherein said host cell is a yeast cell or a bacterial cell.

8. The host cell of claim 6 wherein said host cell is a cell of species *Saccharomyces*, a cell of species *Schizosaccharomyces*, an *Escherichia coli* cell, or a *Salmonella typhimurium* cell.

9. The host cell of claim 6 wherein said host cell is a yeast cell.

* * * * *